(12) United States Patent
Nakao

(10) Patent No.: US 7,722,549 B2
(45) Date of Patent: May 25, 2010

(54) ROTATING FINE NEEDLE FOR CORE TISSUE SAMPLING

(75) Inventor: Naomi L. Nakao, New York, NY (US)

(73) Assignee: Granit Medical Innovations, LLC, New York, NY (US)

(*) Notice: Subject to any disclaimer, the term of this patent is extended or adjusted under 35 U.S.C. 154(b) by 409 days.

(21) Appl. No.: 11/289,657

(22) Filed: Nov. 29, 2005

(65) Prior Publication Data

US 2006/0116605 A1 Jun. 1, 2006

Related U.S. Application Data

(60) Provisional application No. 60/631,348, filed on Nov. 29, 2004.

(51) Int. Cl.
*A61B 10/00* (2006.01)

(52) U.S. Cl. .................. 600/564; 600/565; 600/566; 600/567

(58) Field of Classification Search ......... 600/566–567; 604/22
See application file for complete search history.

(56) References Cited

U.S. PATENT DOCUMENTS

| | | | | |
|---|---|---|---|---|
| 4,099,518 A | * | 7/1978 | Baylis et al. ............... | 600/567 |
| 4,314,560 A | * | 2/1982 | Helfgott et al. ............. | 606/171 |
| 4,644,952 A | * | 2/1987 | Patipa et al. ............... | 606/167 |
| 5,048,538 A | * | 9/1991 | Terwilliger et al. ......... | 600/567 |
| 5,161,542 A | * | 11/1992 | Palestrant .................. | 600/567 |
| 5,267,572 A | * | 12/1993 | Bucalo ...................... | 600/567 |
| 5,333,619 A | * | 8/1994 | Burgio ....................... | 600/567 |
| 5,336,176 A | * | 8/1994 | Yoon .......................... | 604/506 |
| 5,423,330 A | * | 6/1995 | Lee ............................ | 600/566 |
| 5,718,237 A | * | 2/1998 | Haaga ........................ | 600/564 |
| 6,102,887 A | * | 8/2000 | Altman ....................... | 604/22 |
| 6,770,070 B1 | | 8/2004 | Balbierz | |
| 7,226,459 B2 | * | 6/2007 | Cesarini et al. ............. | 606/170 |
| 7,252,641 B2 | * | 8/2007 | Thompson et al. .......... | 600/568 |
| 7,278,970 B2 | * | 10/2007 | Goldenberg ................ | 600/564 |
| 7,465,278 B2 | * | 12/2008 | Cicenas et al. .............. | 600/565 |
| 2002/0072712 A1 | * | 6/2002 | Nool et al. ............. | 604/167.01 |
| 2005/0090728 A1 | * | 4/2005 | Mest ........................... | 600/373 |
| 2005/0182339 A1 | * | 8/2005 | Lee et al. .................... | 600/564 |

* cited by examiner

*Primary Examiner*—Max Hindenburg
*Assistant Examiner*—Sean P Dougherty
(74) *Attorney, Agent, or Firm*—R. Neil Sudol; Henry D. Coleman; William J. Sapone

(57) ABSTRACT

A medical instrument usable with an ultrasound-endoscope for performing a needle biopsy on a patient's internal body tissues usable at a surgical site not visible to the unaided eye or viewed endoscopically, comprises an elongate tubular member with a hollow needle element connected at its distal end, a sheath member housing said tubular member and needle element, an actuator subassembly with a shifter member operatively connected to elongate tubular member's proximal end, and a distal camming subassembly, said subassembly enabling a rotating motion of said needle member while handle actuator is moved in the forward direction. Upon inserting an ultrasound-endoscope into a patient and locating a mass, the fine needle with sharply pointed spoon shaped distal end is inserted into the mass aided by endoscopic and ultrasonographic guidance. Once in the mass, a camming action is initiated, causing rotation of the fine needle within the mass, resulting in a scooped out core biopsy. This instrument enables the performance of a fine needle aspiration requiring only one or two needle introductions, with a resultant core biopsy substantial enough for diagnostic purposes.

12 Claims, 15 Drawing Sheets

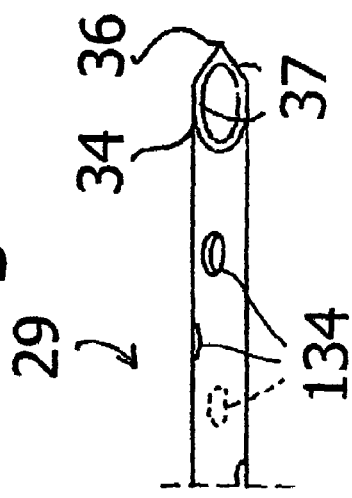
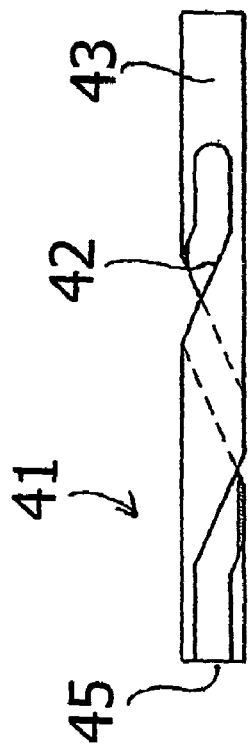
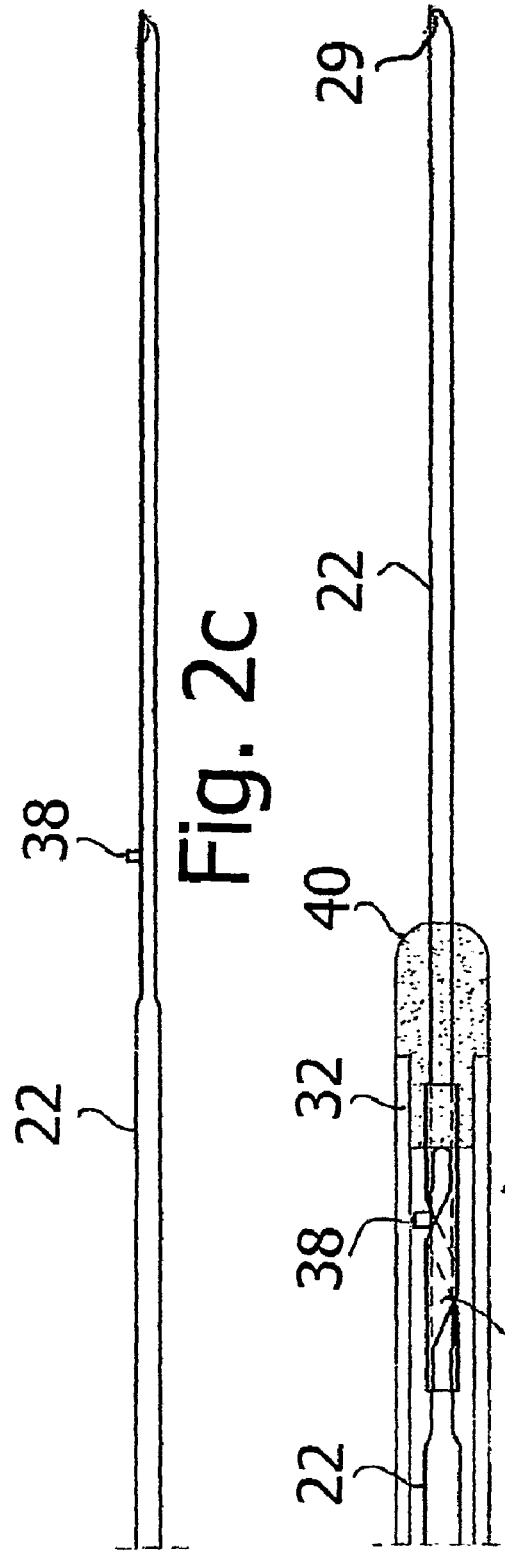

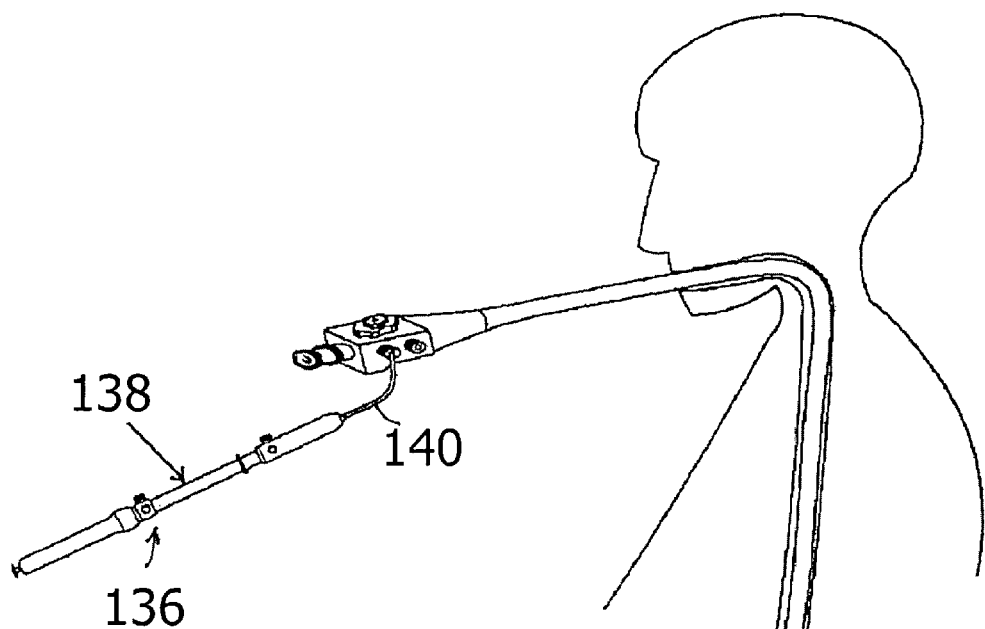
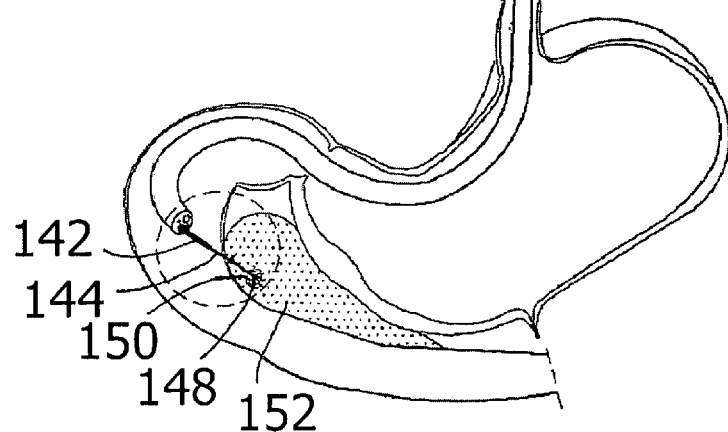
Fig. 15

ROTATING FINE NEEDLE FOR CORE TISSUE SAMPLING

CROSS-REFERENCE TO RELATED APPLICATION

This application claims the benefit of U.S. Provisional Patent Application No. 60/631,348 filed Nov. 29, 2004.

FIELD OF THE INVENTION

This invention relates to a medical instrument for use in the application of tissue sampling. An instrument in accordance with this invention is usable with ultrasound, and in some cases an ultrasound-endoscope for performing a needle biopsy operation on a patient's internal body tissues at a surgical site not visible to the unaided eye.

BACKGROUND OF THE INVENTION

Fine needle aspiration (FNA) has been a well accepted method for obtaining tissue samples for pathologic or histologic analysis in diagnosing tumors of the pancreas and other soft tissue organs. Endoscopic ultrasound (EUS) and EUS-guided fine needle aspiration (EUS-FNA) have become important tools in the evaluation of pancreatic masses.

Conventional surgical techniques for obtaining tissue samples accessible only through a flexible ultrasound-endoscope using a fine needle generally require numerous needle sticks. These procedures often result in obtaining a small number of cells with each aspiration, cells which may or may not be diagnostic. In addition, such procedures are often traumatic because of the multiple needle passes that it necessitates. This is especially true in the case of pancreatic biopsies. The pancreas secretes digestive enzymes. When injured, these enzymes are released, and may induce self digestion, and necrosis of the pancreas, and adjacent organs. The current technique used during Endoscopic Ultrasound Fine Needle Aspiration (EUS-FNA) of a pancreatic tumor entails the passage of an 18-22 gauge stainless steel needle. This needle is passed through the working channel of a linear echo endoscope under real-time guidance into the endo-sonographically visualized pancreatic mass. The needle is moved back and forth multiple times through the lesion with varying degrees of suction applied to it. The specimens obtained are then deposited onto a cytology slide for immediate fixation, staining and cytopathologic examination.

Aspirating a sample from a fluid medium through a needle is a simple procedure. Aspirating a sample from a solid mass is difficult. Most pancreatic EUS-FNA procedures take up to 30 needle passes to make a definitive cytological diagnosis of pancreatic carcinoma. Oftentimes, the only cells that are obtained are blood cells, or normal pancreatic tissue cells. Even when tumor cells are captured, these are often fragmented, and separated from each other. It is therefore almost impossible to differentiate a primary pancreatic tumor from a metastatic lesion.

Despite the time consuming and traumatic nature of the current FNA procedure, the consequence of a non-diagnostic aspirate is worse, because a missed diagnosis of pancreatic cancer is a sure death sentence. Therefore, if a pancreatic tumor is suspected but the FNA result is negative, the patient must then undergo a pancreatic biopsy through an abdominal incision. Although needles for taking core biopsies of internal organs exist, these needles are much thicker than the needles used during fine tissue aspiration. An example of such a needle is the Mangini needle, with which percutanious liver biopsies are used. In order to introduce this needle into the liver, an incision must be made in the skin with the sharp tip of a scalpel. The needle is then pushed into the incision, and under aspiration is quickly pushed in and out of the liver with a quick stabbing motion. The resulting core biopsy is almost always diagnostic, and ample to examine sheets of tissue cells representative of the pathology that is sought. The injury, however, is much greater than that inflicted with a fine needle.

The choices for obtaining diagnostic tissue from internal organs are three fold. The first choice is to obtain a biopsy though an open operative incision or a laparoscopic technique, which entails surgical intervention. The second option is to use a large diameter stiff stainless steel needle. This method may only be used for lesions that are near the exterior of the body, such as described above in relation to the Mangini needle. The third method is to obtain cells through a fine needle with ultrasound guidance. While this method is least traumatic with only one needle introduction, it produces a poor yield of diagnostic material. In the best case scenario, and after multiple needle sticks, several cells of the tumor are retrieved. Because the cells are obtained separate from one another, they are examined by the pathologist without their spatial relationship to the rest of the organ that they originated from. In the worst case, even these tumor cells are not obtained, only blood cells and normal tissue, necessitating one of the more invasive procedures. It is therefore most desirable to have an instrument of being passed through the flexible endoscope that is both delicate so as not to traumatize the area that is being biopsied, and at the same time be capable of obtaining a core tissue biopsy that will be diagnostic. It would be of great advantage if diagnostic certainty could be achieved with a minimal number of instrument passes, thus achieving excellent results with minimal trauma to the patient.

The fine needle aspiration technique is also widely used to obtain cells from suspected lesions in organs that are more superficial. These organs include breast, prostate, thyroid and parathyroid. Although these organs are more accessible to the needle than the pancreas, the trauma incurred by a thick core biopsy needle stick is great. Millions of women undergo fine needle aspirations for suspected breast cancer. Here too, 10-15 needle sticks are required to obtain what is deemed a sufficient number of cells for an adequate specimen.

When a woman comes for such a biopsy, she is anxious and afraid of the impending diagnosis. Oftentimes she leaves the procedure with a large hematoma, an internal blood-clot in a severely bruised breast, resulting from the numerous needle sticks required to obtain cells. Recently, a biopsy gun has been introduced for this purpose. The gun is equipped with a thicker needle, spring loaded to jump out of the instrument, and into the suspected lesion. This method has rendered many women even more anxious. A short, inflexible fine needle, one of the same diameter as the fine needle currently used for aspiration, would be of great benefit if it would enable a single needle pass into an organ such as the breast, and obtain a core biopsy on one relatively atraumatic needle pass.

OBJECTS OF THE INVENTION

An object of the present invention is to provide an improved medical instrument for the removal of tissue samples for diagnostic purposes though a fine needle.

A more specific object of the present invention is to provide an instrument assembly and a related method for collecting a core tissue biopsy.

A related object of the present invention is to provide a needle assembly that requires only a minimal number of needle passes into the organ tissue.

A further object of the invention is to obtain all the above-mentioned benefits and still use a needle of the same small gauge as is currently used in the state of the art of the fine needle aspiration technique, so as not to cause undue trauma to the pancreas or other internal organs that are sampled.

Another object of the invention is to provide an instrument for more superficial organ lesions such as breast, with a needle that is as thin as the fine needle currently used for aspiration, but enabling only a single passage with a resultant core biopsy.

Another object of this invention is to provide such an instrument which is easy to use and can accomplish the desired result in a short period of time, while being cost effective.

These and other objects of the invention will be apparent from the drawings and descriptions herein. Although every object of the invention is deemed to have been met by at least one embodiment of the invention, there is not necessarily any one embodiment that achieves all of the objects of the invention.

SUMMARY OF THE INVENTION

This invention enables in part the performance of a fine needle aspiration requiring only one or two needle passes, with resultant tissue sampling which is more substantial, providing the opportunity for a definitive diagnosis.

A method for obtaining a coring needle biopsy from selected portions of internal body tissues of a patient utilizes a flexible hollow tubular shaft member, preferably of a metal material, with a needle shaped at its most distal end, the tubular shaft member being slidably disposed within an outer sheath member. The outer sheath member has a diameter sufficiently small to enable its insertion into the working channel of a flexible endoscope. In one embodiment of the invention, the outer sheath member is reinforced by means of a metal coil embedded into the sheath's wall. While the outer sheath member may be made of Teflon, or PTFE, the metal coil or otherwise braided reinforcement may be made of stainless steel, or a shape memory metal such as Nitinol. This reinforcement by a metal coil or otherwise braided structure renders the outer sheath sturdy, yet flexible. This feature supports the actuation of the elongated inner metal needle.

The inner flexible hollow tubular member may be made of stainless steel, or a shape memory metal such as Nitinol. While being flexible enough to pass through an elongated flexible endoscope, it is also sturdy enough to provide the required stiffness to form the distal needle enabling introduction into the organ requiring tissue sampling. This inner metal shaft member is slidably disposed within the outer sheath member, occupying all, or almost all of the length of the outer sheath member, terminating at its distal end with a specially shaped needle to be discussed further herein below. An actuator sub-assembly is operatively connected to the proximal end of the inner tubular shaft member. When actuated, the handle assembly pushes the elongate needle, or inner tubular shaft member with distal needle shape, in and out of the outer sheath.

A camming subassembly is provided preferably in the handle subassembly for converting a linear motion of the inner tubular shaft member, applied proximally by the operator, at least partially into a rotating motion of the distal end of the inner tubular shaft member. When the distal end is shaped in the special needle design, this rotation facilitates the collection of a tissue core biopsy. The elongate inner tubular shaft member may be provided with a syringe attachment port at its proximal end, the syringe port communicating with the lumen of this tubular member. In addition, a stainless steel, Nitinol, or other metal guide wire may be passed through the inner tubular shaft member with distal needle shape, in order to further stabilize it while piercing tissue. The guide-wire's most distal end may be shaped as a needle as well.

According to a more specific feature of the present invention, the distal needle-shaped end of the inner tubular shaft member is configured as a spoon not unlike the shape of an ice-cream scooper. The distal spoon-shaped needle end is provided with a sharp piercing tip, and very sharp edges extending from the needle tip or point. Located on the proximal portion of the inner tubular member, near or internal to the handle sub-assembly, is a key element in the form of a laterally or transversely extending stub or a spiral flange or rib. In addition, the handle sub-assembly includes a short metal pipe or tube provided with a spiral cutout or groove along which the key element slides during at least a portion of a distally directed motion of the inner tubular shaft member. The short metal pipe or tube is disposed at a proximal location inside the handle assembly, affixed to the handle assembly. The elongated needle is slidably disposed within the catheter or sheath, capable of passing freely through it.

The spiral groove or track and the key element inserted into the groove or track function as a camming mechanism, which converts a linear translation into a rotary motion. This feature provides for the turning motion of the entire inner tubular shaft member and consequently its needle shaped distal end, for capturing the desired tissue sample.

A method for obtaining a core biopsy specimen from tissue not accessible to endoscopic visualization comprises, in accordance with the present invention, the steps of (a) inserting an endoscope equipped with an ultrasound assembly into a patient, and advancing it intraluminally towards the area that lies closest to the organ wherein a lesion is suspected, (b) using the endoscope-ultrasound assembly to project ultrasonic vibrations from the endoscope into extraluminal organs to visually inspect the suspected lesion on an exterior screen, (c) delineating the suspicious lesion or tissue mass ultrasonographically, (d) moving the sheath member of the invention in a distal direction through a working channel of an endoscope to eject the sheath member from the working channel, (e) after detecting the lesion or tissue mass ultrasonographically, shifting an actuator slider in a distal direction to thereby eject the inner tubular shaft member needle element from the sheath member, the needle element being an integral part of the inner the inner tubular shaft member (f) piercing an intestinal wall with the needle element under endoscopic guidance, (g) manipulating the needle element in the direction of the lesion or tissue mass under ultrasonographic guidance, (h) inserting a distal end portion of the needle element into the lesion or tissue mass under ultrasonographic guidance, (i) upon the inserting of the needle element to an apt location in the lesion or tissue mass for biopsy, pushing the last part of the needle from its proximal end, thereby initiating an automatic rotating, or camming action at its distal end, resulting in the capture of a core tissue biopsy of tissues at the location, (j) withdrawing the inner tubular shaft member with distal needle shape back into the outer sheath while applying suction to a proximally located port in order to bring the core biopsy specimen deeper into the needle for withdrawal, (k) withdrawing the instrument from the endoscope's biopsy channel, and (k) depositing the captured core biopsy into preservative by flushing it with an injection of fluid delivered from the inlet at the handle assembly.

The present invention contemplates that the needle element, of whatever configuration, is connectable to a source of electrical current for effectuating a cauterization of internal tissues during passage of the instrument through the tissues. Such a cauterization feature facilitates penetration of the needle element into or through hard internal tissues that form a capsule about soft tissues. Without the cauterization capability, attempting to push the needle through the capsule into the soft tissues typically results in a mere deformation of the capsulated tissues, preventing penetration of the needle element.

The present invention contemplates that there may be a guide wire that is inserted into the inner tubular shaft member. This shaft member is made of a solid flexible material such as stainless steel, or preferably Nitinol. The guide wire provides further stability and firmness to the needle, especially when it is passed through an intestinal wall, and into a capsule of an organ.

The present invention additionally contemplates that the needle is provided along at least a portion of its length with a plurality of longitudinally spaced apertures for the dispensing of a liquid solution into internal tissues. The apertures may also be staggered circumferentially about the needle element.

A method for obtaining a needle biopsy from selected portions of internal body tissues of a patient utilizes, in accordance with another embodiment of the present invention, a flexible hollow tubular member provided at a distal ed with a hollow needle tip, the tubular member and needle being disposed in an outer sheath member. The outer sheath member has a diameter sufficiently small to enable its insertion into the working channel of a flexible endoscope. An actuator sub-assembly is operatively connected to the hollow tubular member's proximal end so as to allow the tubular member with distally connected needle to be ejected from the outer sheath member or catheter. A camming subassembly is included for converting a linear motion of the tubular member partially into a rotating motion of the needle element. This rotation facilitates the collection of a core biopsy. The elongate tubular member may be provided with a syringe attachment port at its proximal end, the syringe port communicating with the lumen of the tubular member.

According to a more specific feature of the present invention, the needle's distal end is configured in the shape of a spoon with a sharp piercing tip and sharp edges extending proximally from the needle tip. Located on the proximal portion of the needle-shaft is a small stub element. In addition, the distal sub-assembly includes a short metal tube, the tube provided with a spiral cutout. The short metal tube is disposed in a fixed state at a distal location of the catheter, affixed to an outer metal collet, the collet providing the most distal portion of the catheter. The needle which is slidably disposed within the catheter is capable of passing freely through the metal tube.

Alternatively, the camming mechanism includes a spiral groove or track and a key inserted into the groove or track and may be located at a proximal end of the instrument, within an actuator handle.

According to a further feature of the present invention, the key element (stub, rib, flange) engages with the proximal aspect of the short metal tube's spiral cutout. A tactile sensation perceived by the operator holding the actuating handle occurs when the needle's stub hits the metal tube. At this point it is necessary to manipulate the handle slightly in order to engage the stub into the cutout. Once engaged, additional forward advancement of the actuator will initiate a rotation of the needle (a camming action) within the tumor mass, "scooping out" a core biopsy specimen with the spoon shaped needle's end. This process is visualized both endoscopically and ultrasonographically. Once a core biopsy has been obtained, a syringe is attached to the proximally located port, and aspirated to bring the core biopsy into the needle's lumen. The needle is then withdrawn into the sheath, and the entire assembly is extracted from the biopsy channel of the endoscope. The specimen is then ejected into preservative solution or onto a slide by injecting fluid through the port.

Another embodiment of the present invention provides a rotatable fine needle for obtaining core biopsy tissue from more superficially located organs with a suspected mass lesion. The needle length is contemplated to be about the same as that of a fine needle currently used for aspiration of cells. Its distal end is spoon shaped, similar to that of the endoscopic core biopsy fine needle. The camming mechanism is preferably located in the handle in this instrument as well. Because the handle assembly includes the camming mechanism, it is longer than the handle used in a needle that is attached to a syringe only. It is not ergonomically comfortable to hold such a long handle assembly with a thumb ring being located on the proximal end of the handle. Therefore, in accordance with the present invention, the instrument is provided with a handle assembly wherein the thumb ring is attached on a lateral aspect of the handle, rather than at its most proximal end. A grip for the fingers is provided more distally on the handle, in the shape of a spool, being further elucidated in the drawings, and described below. In addition, an interchangeable thumb ring and syringe attachment is provided for the shorter needles, also further described herein below.

A method for obtaining a core biopsy specimen from a more superficial organ such as breast comprises, in accordance with the present invention, the steps of (a) using an external ultrasound probe to localize and delineate a suspected mass lesion in a patient, (b) inserting a needle through the patient's skin, and pushing the needle towards and into the mass lesion under ultrasound guidance, (c) shifting an actuator slider in a distal direction, thereby engaging a camming mechanism to cause a tip of the needle to rotate 360 degrees within the mass lesion, thereby severing a tissue sample from the mass lesion, (d) aspirating the tissue sample deeper into the needle using a syringe attached to a proximal end of tne needle, (e) removing the needle from the tissue, and (f) injecting a liquid through the needle causing the core biopsy to be ejected into the preservative solution.

BRIEF DESCRIPTION OF THE DRAWINGS

FIG. 2A is a side elevational view, on an enlarged scale, of a camming collar or tube provided at the distal end of the endoscopic instrument assembly of FIG. 1.

FIG. 2B is a side elevational view, on an enlarged scale, of a distal tip of a needle element of the endoscopic instrument assembly of FIG. 1.

FIG. 2C is a side elevational view, on a smaller scale, of a distal end portion of the needle element of FIG. 2B, showing the needle element provided with a laterally projecting guide stub.

FIG. 2D is a partial longitudinal cross-sectional view of the distal end portion of the endscopic instrument assembly of FIG. 1, showing the components of FIGS. 2A-2C.

FIG. 15 is a schematic view of an upper portion of a person's digestive tract, showing a step in an endoscopic procedure pursuant to the present invention.

DETAILED DESCRIPTION

Figure 1:
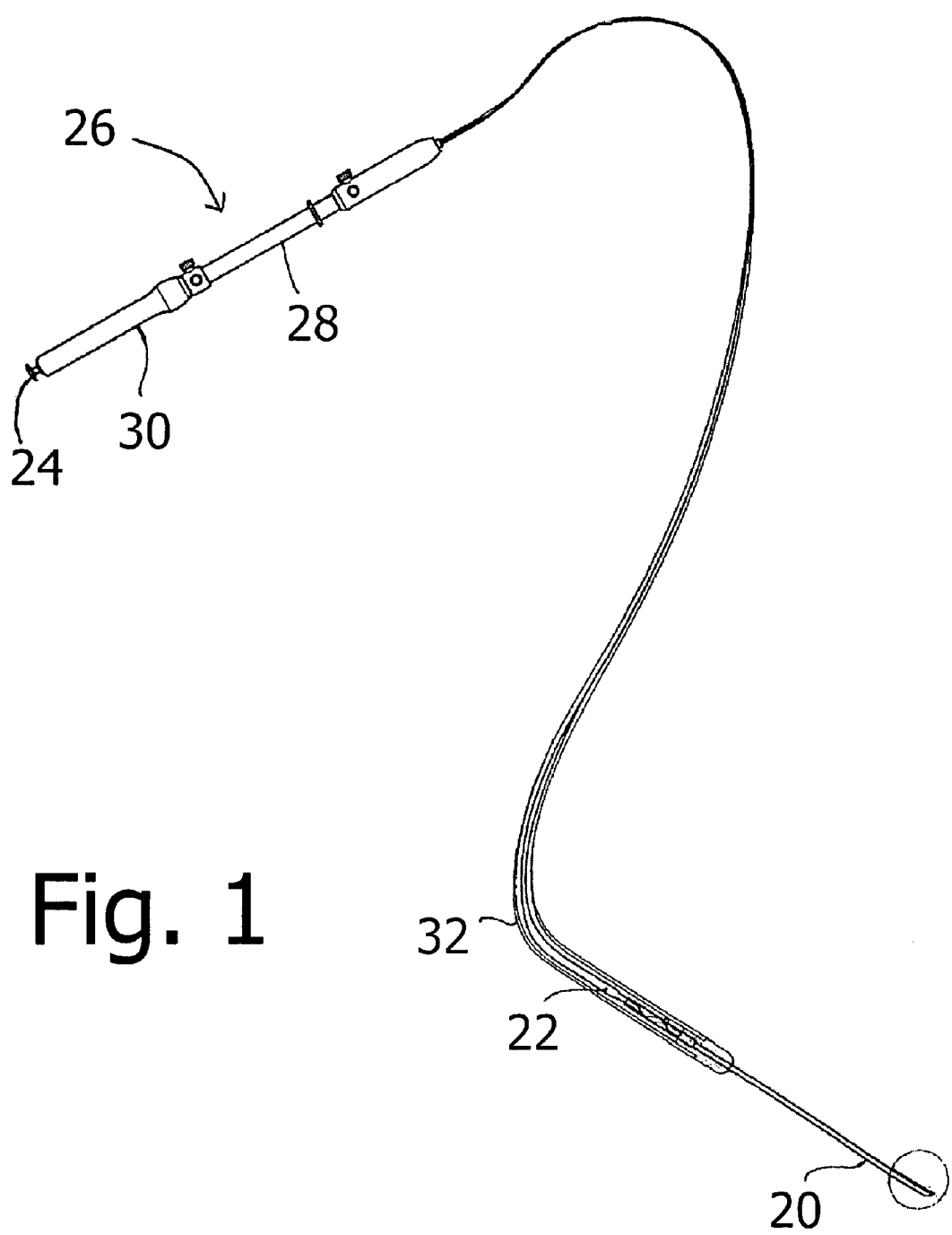
FIG. 1 is a schematic perspective view of an endoscopic instrument assembly in accordance with the present invention.

As illustrated in FIG. 1, a medical instrument assembly for use in procedures for obtaining tissue samples comprises a hollow needle element 20 communicating with a lumen (not shown) of a tubular shaft member 22 to enable suction of a patient's tissue to be obtained by needle 20. Tubular shaft member 22 is provided at a proximal end with a port 24 that communicates with the lumen of the tubular shaft member. As disclosed below with reference to other embodiments, needle element 20 may be an integral distal tip of shaft member 22.

The instrument assembly of FIG. 1 includes an actuator subassembly 26 including a cylindrical body portion 28 carrying a slidably mounted shifter 30. Shifter is connected to tubular shaft member 22 for moving the tubular shaft member alternatively in the distal direction and the proximal direction through a flexible tubular sheath 32 that is fixed at a proximal end to cylindrical body portion 28. Sheath 32 has a sufficiently small diameter to enable insertion of the sheath, together with tubular shaft member 22 into a biopsy channel 61 of an endoscope insertion member 46, both shown in FIG. 3.

Needle element 20 is made of a super-elastic material such as Nitinol. Needle element 20 has a predetermined rest configuration, usually straight. The application of an external force of a limited magnitude to the needle element 20 may deform it out of the rest configuration and into another configuration. Needle element 20 will however spring back to its straight or other predetermined configuration upon cessation or termination of the external force.

Sheath member 32 is made of a polymeric material such as PTFE (Teflon™) reinforced by means of a metal coil embedded into the sheath's wall. The metal coil or otherwise braided reinforcement may be made of stainless steel or a shape memory metal such as Nitinol. This reinforcement by a metal coil or otherwise braided structure renders the outer sheath 32 sturdy yet flexible and supports the actuation of the elongated inner metal needle 20. As shown in FIGS. 2A-2D, needle element 20 possesses a distal end configured in the shape of a spoon 34 with a sharp piercing tip or point 36. Spoon 34 may be provided with sharp curved lateral edges 37 for facilitating the cutting of internal body tissues during an endoscopic biopsy operation. Spoon 34 may be formed in part by beveling the end of the tubular shaft member. A camming mechanism may be provided at the distal end of sheath 32. The camming mechanism includes a key element or cam follower at the proximal end of needle element 20 in the form of a small laterally or transversely extending stub 38. Proximally to stub 38, needle element 20 widens into tubular shaft structure 22 also made of flexible material which may or may not be a similar super-elastic material such as that of needle element 20. Tubular structure 22 may be made of stainless steel or a shape memory material such as Nitinol, same as needle element 20. Needle element 20 and tubular structure 22 are housed inside sheath 32. At the distal end of sheath 32 there is a metal collar 40 which is coupled with tubular member 32.

As shown in FIGS. 2A and 2D, a distal subassembly 48 includes a metal tube 41 having a spiral cutout or slot 42. Spiral cutout 42 terminates at the proximal end 45 of metal tube 41 and is spaced from the distal end 43 of metal tube 41.

Needle element 20 has a distal end 29 in the form of spoon 34 with the spoon's distal end tapering to a sharp tip or point 36.

FIG. 2D shows subassembly 48 assembled in its functioning configuration. As shown, stub 38 is fitted within spiral cutout 42 of metal tube 41. Metal tube 41 is coupled with and partially contained inside metal collar 40 and extends in a proximal direction into sheath 32.

Figure 3:
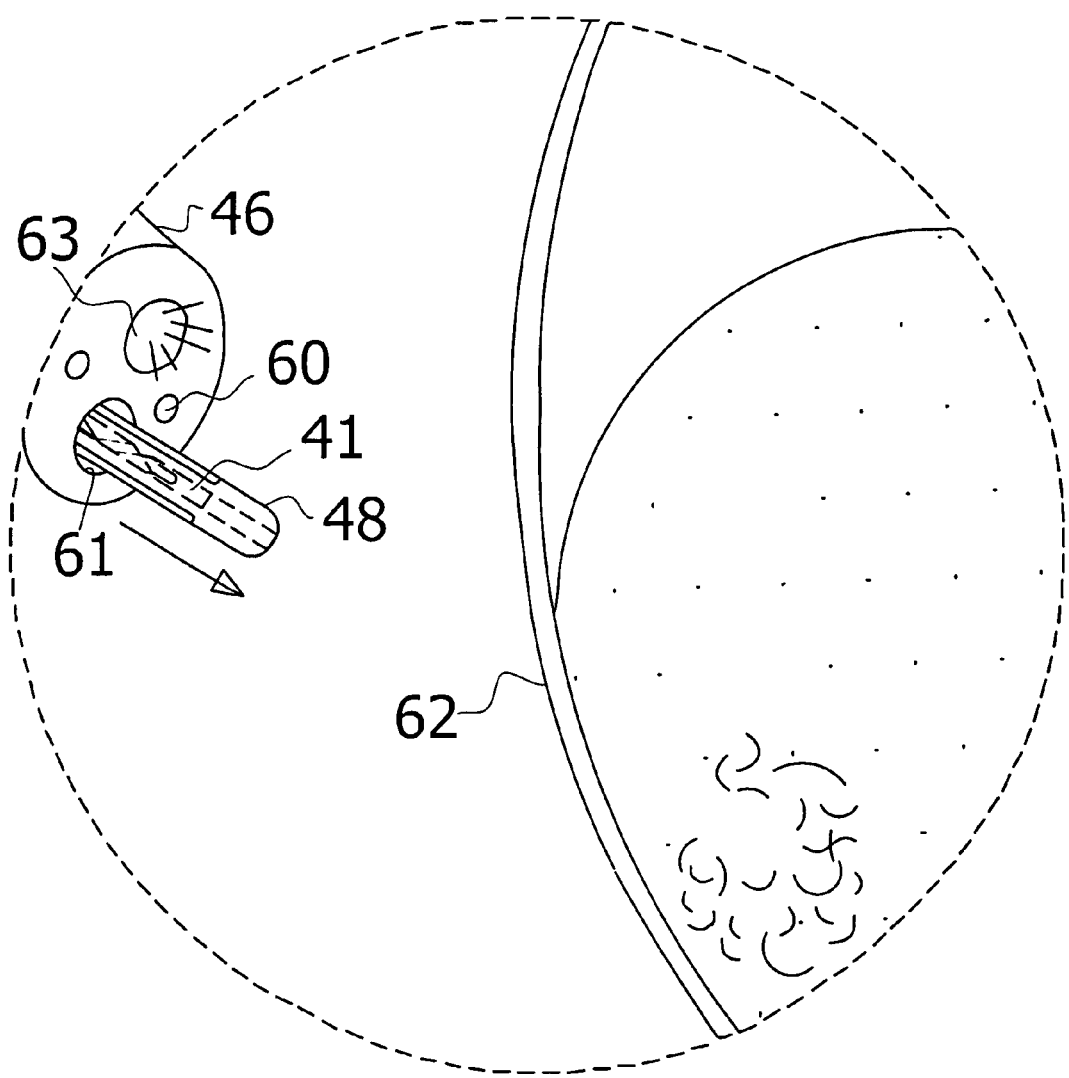
FIG. 3 is a schematic perspective view of the distal portion of the assembly of FIG. 1 in a pre-deployment position, as introduced through a flexible endoscope.
Figure 4:
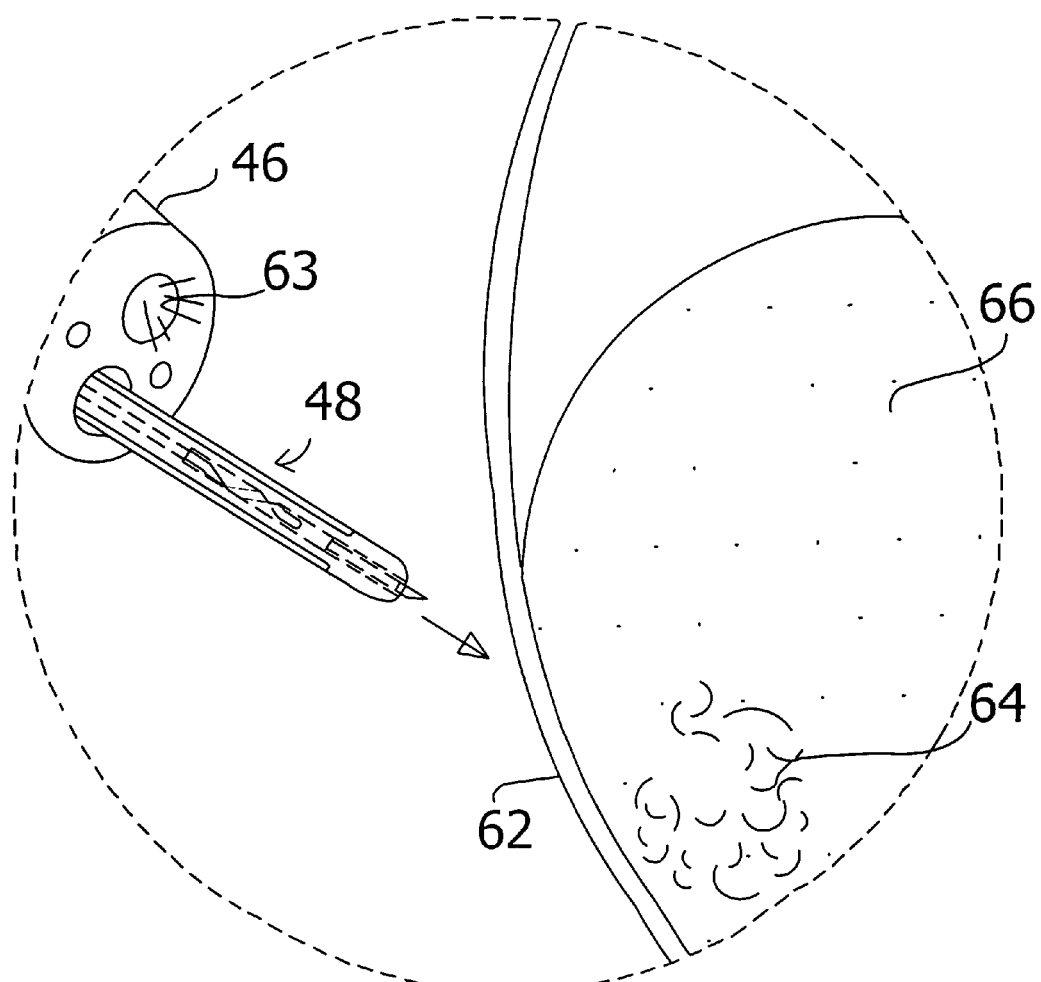
FIG. 4 is a schematic perspective of the distal portion of the assembly of FIG. 1 with the needle element of FIGS. 2B-2D starting to be deployed from its housing.
Figure 5:
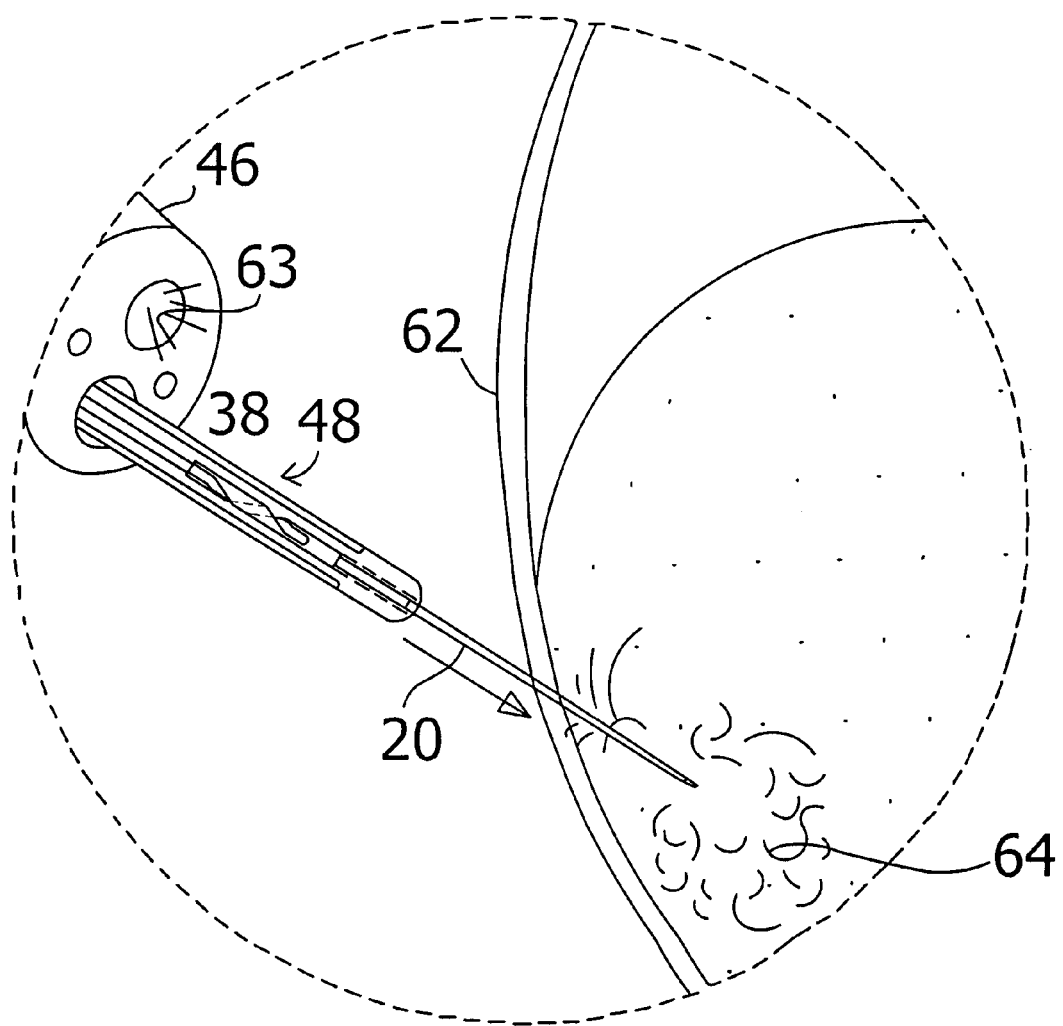
FIG. 5 is a schematic perspective view of the needle of FIG. 4 being deployed from its housing and introduced into a patient's body tissue.

The configuration of distal subassembly 48 is designed to optimize the utilization of the instrument assembly of FIG. 1 in obtaining a core biopsy possibly indicative of a tumor growth from an internal body organ or tissue. As shown in FIG. 15, endoscope insertion member 46 is inserted through a patient's mouth, through the esophagus and stomach into the duodenum. As shown in FIG. 3, insertion member 46 is provided with optical elements such as a lens 60 to enable visual inspection of an inner wall 62 of the duodenum and a light source 63 to illuminate these internal body parts. As shown in FIG. 4, when a mass 64 is detected in the pancreas 66 with an ultrasound device (not shown) attached to endoscope 46, needle element 20 is ejected from subassembly 48 by manipulating actuator subassembly 26 (FIG. 1) in the distal direction. As shown in FIG. 5, needle element 20 is introduced through duodenal wall 62 in the direction of mass 64.

Figure 6:
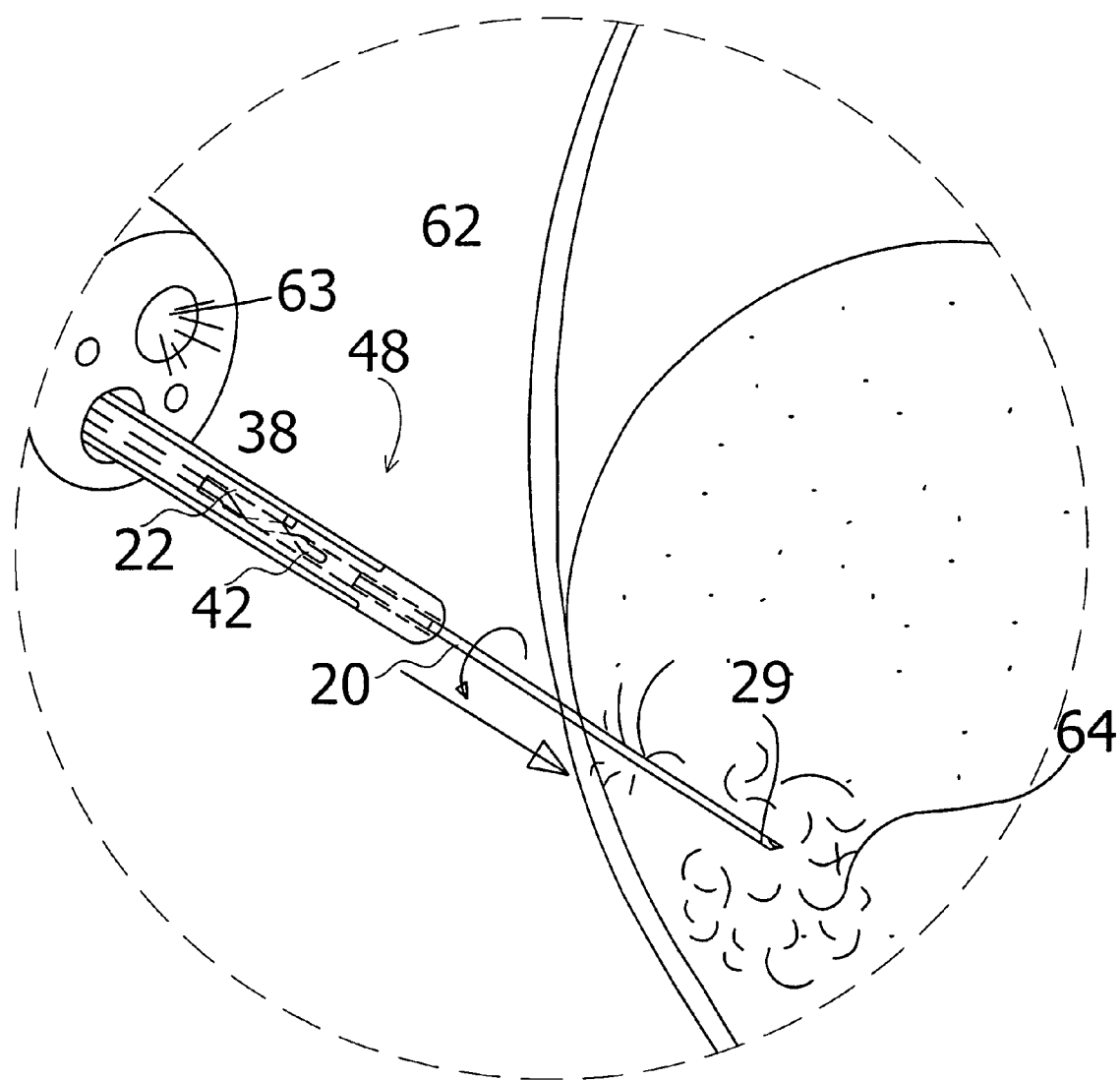
FIG. 6 is a schematic view of the needle of FIGS. 4 and 5 interacting with a threaded collar so as to be turned inside the patient's tissue to obtain a core biopsy.
Figure 7:
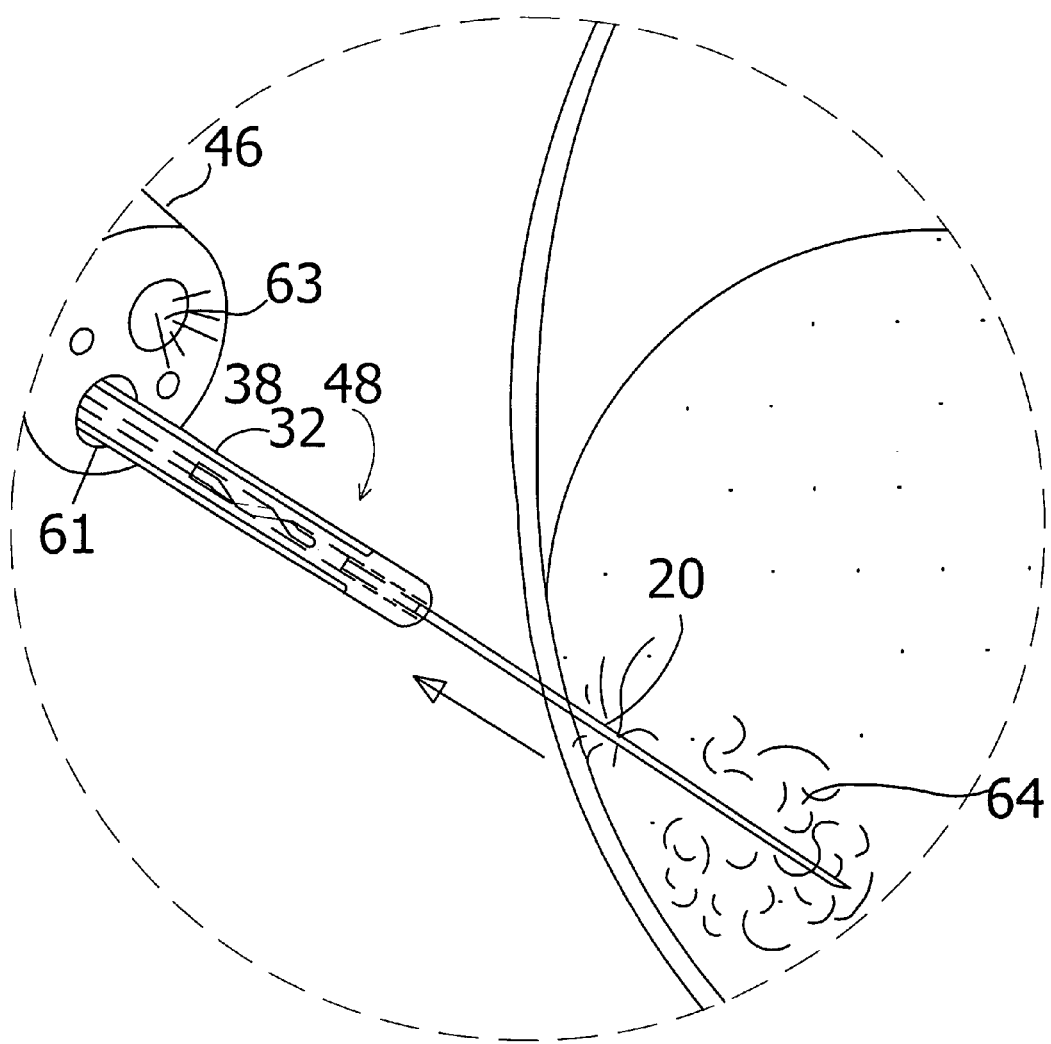
FIG. 7 is a schematic view of the needle being withdrawn into its housing with the specimen inside.

During an initial distal movement of needle element 20, stub 38 is spaced from slotted metal tube 41. As shown in FIG. 6, when needle element 20 reaches the interior of mass 64, illustrated in an ultrasound picture (not shown), continued pushing of needle element 20 engages stub 38 into spiral cutout 42 of metal tube 41. Further distal pushing of needle element 20 now induces needle element 20 to rotate inside tumor 64 due to a camming action of stub 38 against edges or surfaces of spiral cutout 42 in metal tube 41. This camming action causes the sharp spoon shaped distal tip or point 29 of needle element 20 and edges 37 to scoop out a core of tissue from tumor 64. Upon obtaining a core biopsy, a syringe (not shown) is attached to port 24 and operated to aspirate the tissue sample into the lumen of needle element 20. Once the aspiration procedure is completed, needle element 20 is retracted into sheath 32 (FIG. 7), and the entire assembly is withdrawn from biopsy channel 61 of endoscope 46. The specimen is then ejected into preservative by injecting fluid through port 24 into the lumen of tubular shaft member 22 and needle element 20.

The camming subassembly (tube 14, spiral cutout 42, stub or follower 38) is a structural arrangement for converting a linear motion partially into a rotary motion and may be located at any position along tubular shaft member 22, particularly inside actuator subassembly 26. Such an alternative design is depicted in FIGS. 8-11.

Figure 8:
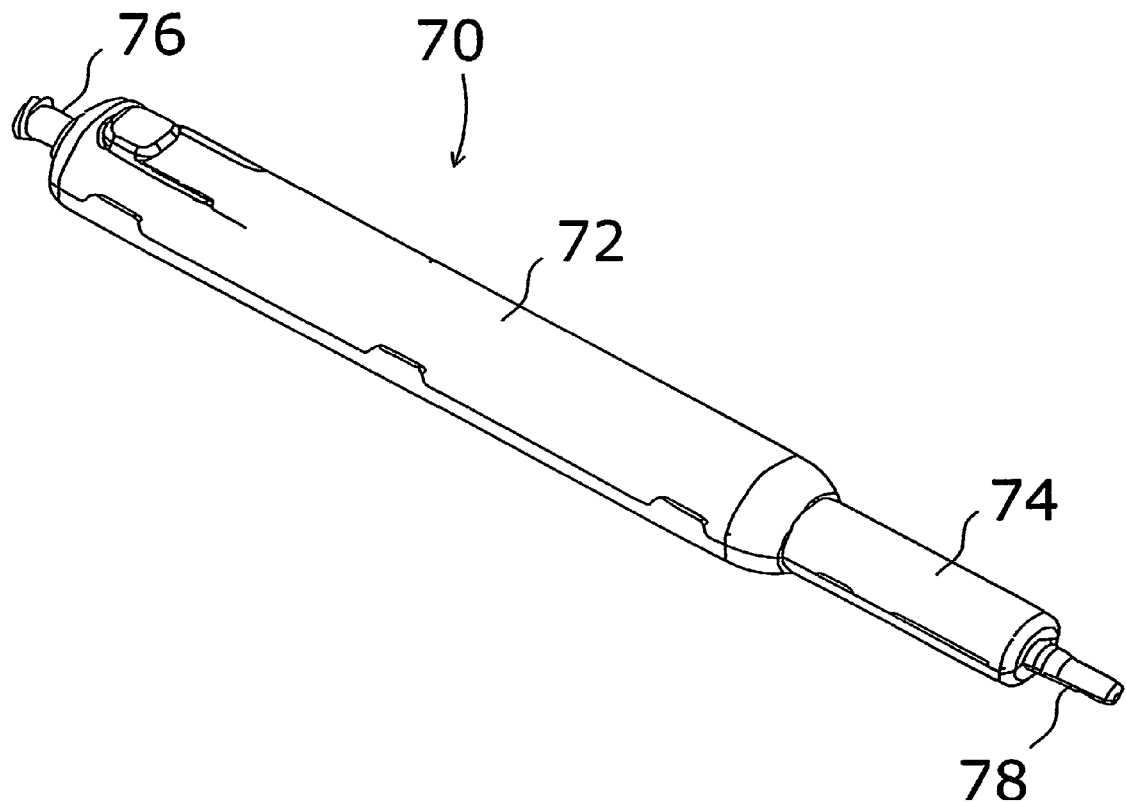
FIG. 8 is a schematic perspective view of a handle or actuator assembly of another embodiment of an endoscopic instrument assembly for core tissue sampling, in accordance with the present invention.
Figure 9:
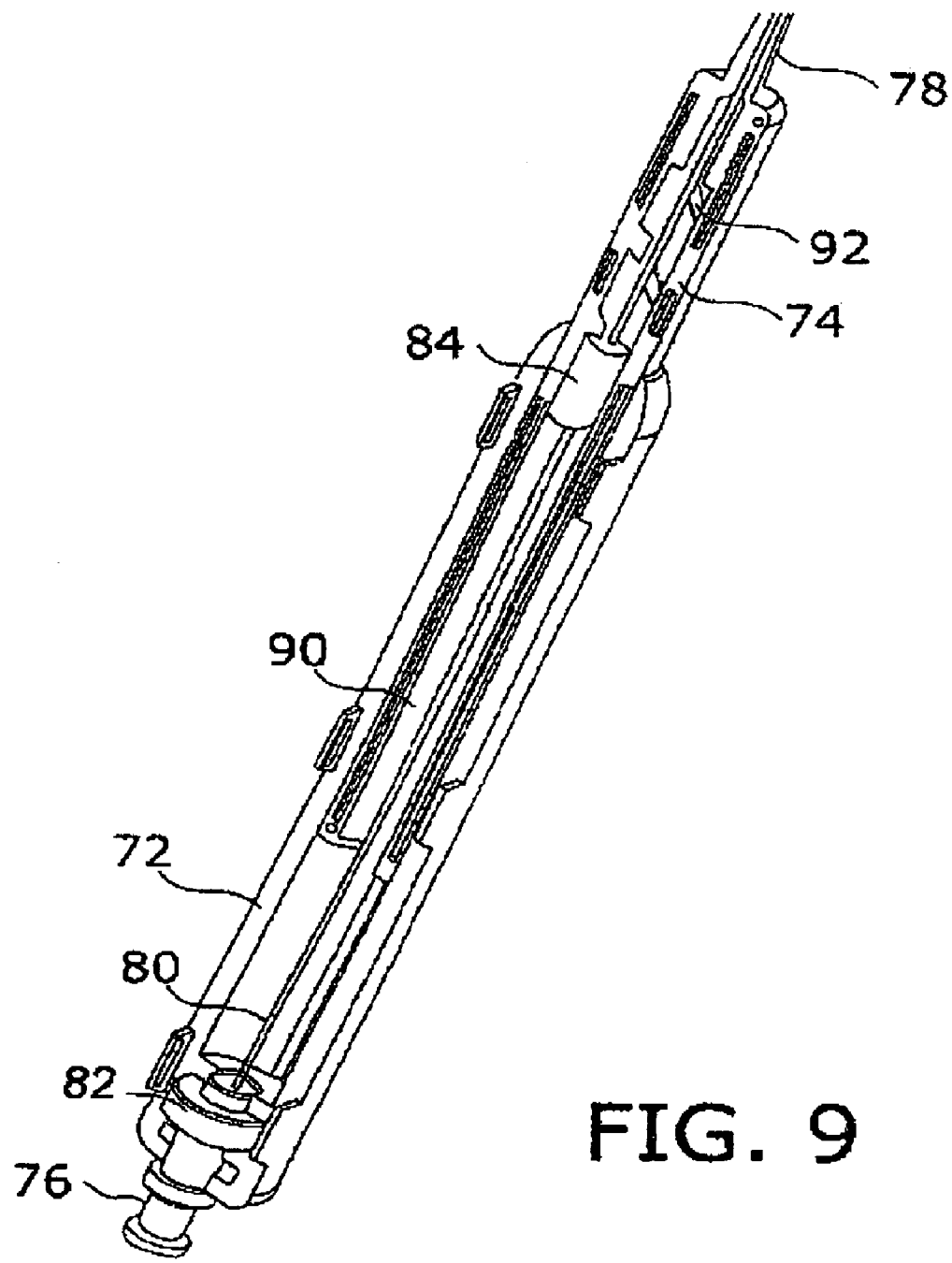
FIG. 9 is a longitudinal cross-sectional, on an enlarged scale, of the handle or actuator assembly of FIG. 8.
Figure 10:
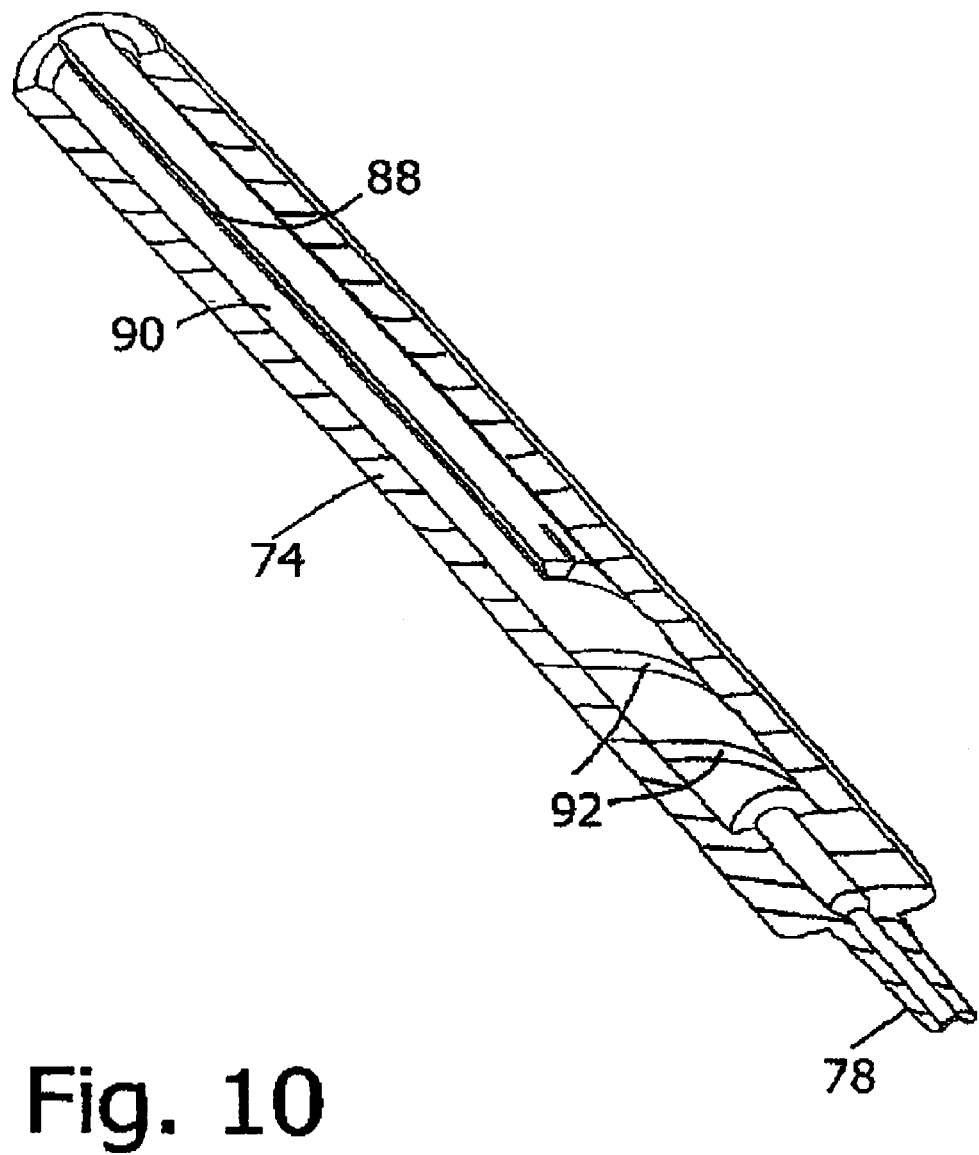
FIG. 10 is a longitudinal cross-sectional view, on a scale smaller than that of FIG. 9, of a slotted or grooved metal plunger tube included in the handle or actuator assembly of FIGS. 8 and 9.

FIGS. 8-10 depict a handle or actuator assembly 70 of a core tissue sampling instrument that may be used in an endoscopic procedure utilizing optics alone or optics in conjunction with endoscopic ultrasonography. Such an instrument includes a flexible sheath member and a flexible shaft member as discussed above. Alternatively, handle or actuator assembly 70 may be part of a breast biopsy instrument having a substantially rigid tubular shaft member, or needle. Preferably, this would be a stainless steel needle. Handle or actuator assembly 70 includes an outer plunger handle or shifter 72 that telescopingly receives, in a distal end, a tubular plunger 74. Plunger handle or housing 72 is provided at a proximal end with a nipple or port element 76 for receiving a nozzle part of a syringe (not shown), while plunger 74 is provided at a distal end with a connector 78 for coupling to a tubular sheath member (not shown).

As shown particularly in FIG. 9, a tubular needle shaft 80 extends through connector 78, plunger 74, and handle or housing 72 and connects at a proximal end to a cap 82 rotatably seated in a cylindrical compartment 84 at the proximal end of plunger handle 72. Needle shaft 80 communicates with nipple or port element 76 via cap 82.

Figure 11:
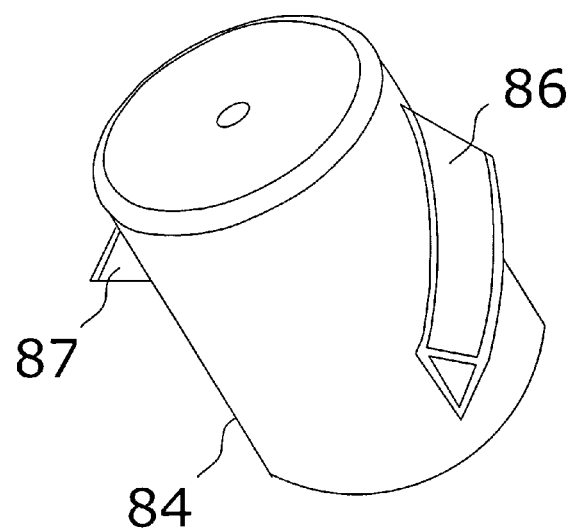
FIG. 11 is perspective view, on a greatly enlarged scale, of a key member or cam follower included in the handle or actuator assembly of FIGS. 8-10.

A cylindrical carrier or stylist 84 on needle shaft 80 exhibits a pair of outwardly projecting spiral rib or flange sections 86, 87 (FIG. 11) serving as keys or cam followers. Spiral rib or flange sections 86, 87 are substantially triangular in cross-section as shown in FIG. 11. A pair of linear grooves or keyways 88 (FIGS. 9 and 10) extend longitudinally along an inner surface 90 of plunger 74 and communicate or intersect at their distal ends with respective spiral cutouts or grooves 92 in inner surface 90 of plunger 74.

During a needle ejection procedure, an operator holds plunger 74 steady or fixed relative to a patient while moving handle or shifter 72 in a distal direction over the plunger. During an initial portion of this distally directed stroke of handle 72, rib or flange sections 86, 87 are each located in and guided by a respective groove or keyway 88 while needle shaft 80 translates distally. As this distal motion of handle 72 continues, rib or flange sections 86, 87 enter respective spiral cutouts or grooves 92 and are constrained to follow those cutouts or grooves, thereby imparting a rotational motion to carrier or stylist 84 and needle shaft 80. Cutouts or grooves 92 thus define camming surfaces, tracks or keyways that convert linear motion of needle shaft 80 at least partially into a rotational motion. At their proximal ends, spiral cutouts or grooves 92 communicate or intersect with linear grooves or keyways 88.

Figure 12:
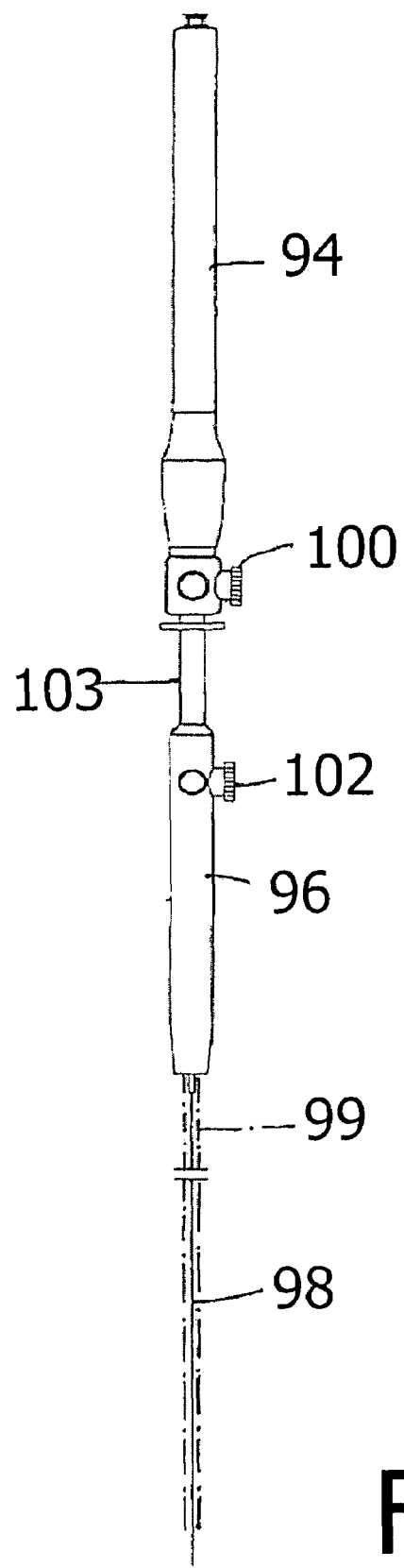
FIG. 12 is a side elevational view, on a reduced scale, of another endoscopic instrument assembly in accordance with the present invention.

FIG. 12 depicts a modified core tissue sampling instrument that incorporates the internal functional elements of the embodiment of FIGS. 8-11. The instrument of FIG. 12 includes a handle or shifter member 94, a plunger member 96 and a tubular needle shaft 98 extending through a tubular sheath member 99. One or more set screws 100, 102 may be provided for fixing plunger 96 relative to handle 94. Plunger member 96 includes a tube 103 that is inserted into handle member 94.

Figure 13:
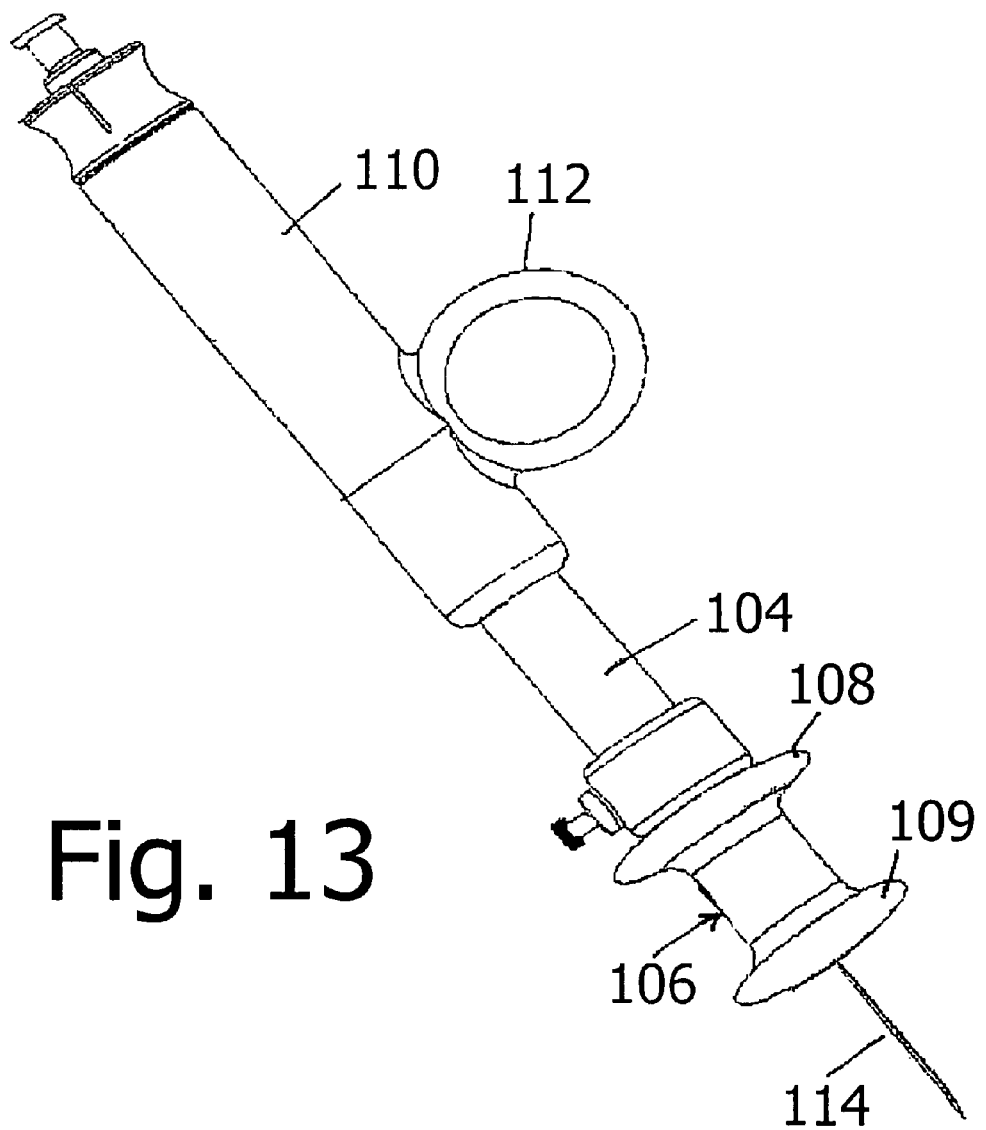
FIG. 13 is a perspective view of a modified handle or actuator assembly of a core tissue sampling instrument in accordance with the present invention.

FIG. 13 depicts another variation of the core tissue sampling instrument of FIGS. 8-11 particularly useful for breast biopsies and core tissue sampling of other superficial orans. Here a plunger part 104 is provided with a spool 106 having a pair of opposed flanges 108 and 109 for receiving a forefinger and a middle finger of a user. An outer tubular handle or shifter member 110 is provided along a lateral surface (not separately designated) with a thumb ring 112. Finger spool 106 and thumb ring 112 enable a user to hold the device and control the movement of a hollow needle shaft 114 with one hand.

Figure 14:
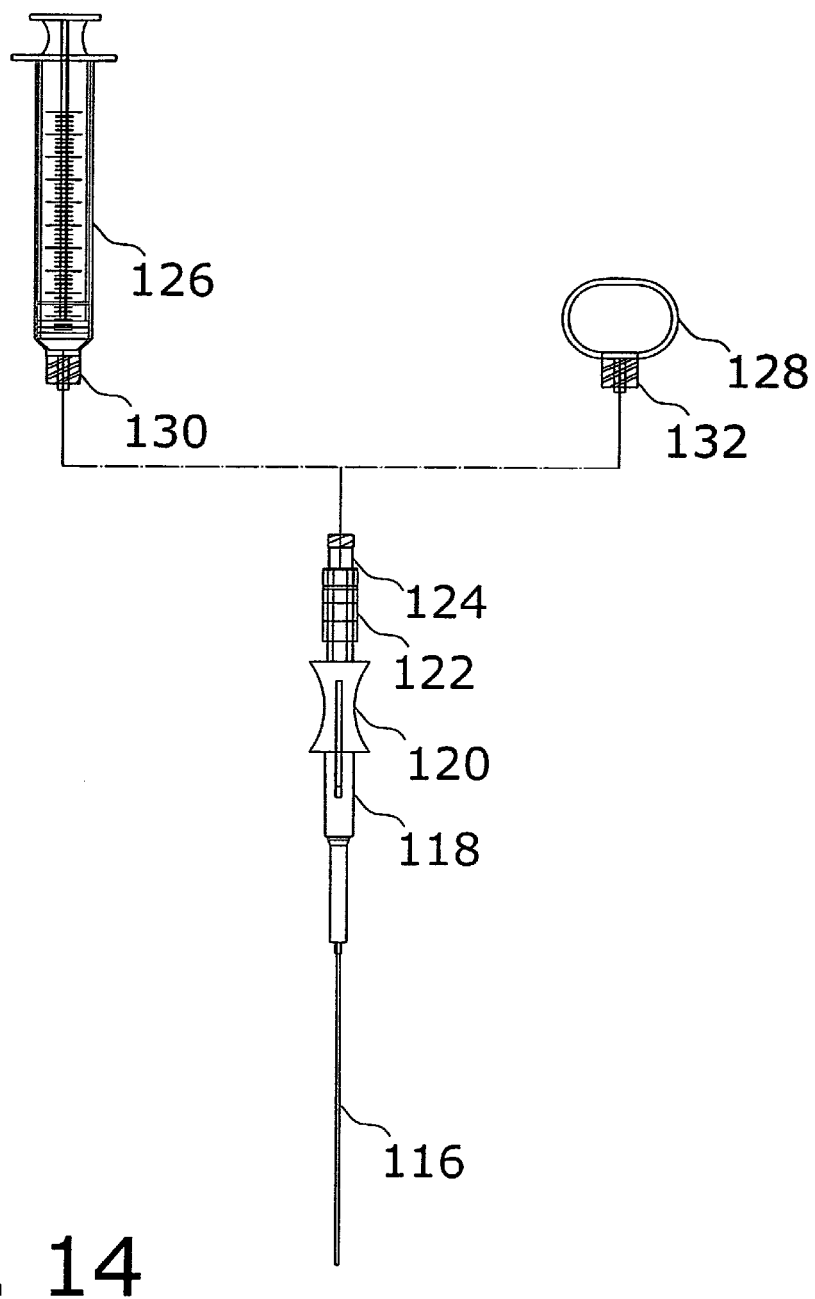
FIG. 14 is a side elevational view of another endoscopic instrument assembly for core tissue sampling, in accordance with the present invention.

FIG. 14 shows yet another variation of the core tissue sampling instrument of FIGS. 8-11. A hollow needle shaft 116 extending through a tubular sheath member 117 is connected to a proximal end of a plunger part 118 that is provided with a finger spool 120. Plunger part 118 is slidably connected to a handle or shifter part 122 provided at a proximal end with an internally threaded screw connector 124 for removably coupling to a syringe 126 and alternatively to a thumb ring 128. Syringe 126 and thumb ring 128 are formed at their distal ends with externally threaded screw connectors 130 and 132 that mate with screw connector 124.

It is to be noted that any of the embodiments of a core tissue sampling instrument described and illustrated herein, particularly including the embodiments of 12-14, may be used with rigid needle shafts, e.g., shafts 98, 114, 116, in a percutaneous tissue sampling procedure. Such a procedure is followed, for example, to extract breast biopsy specimens. The needle shafts 98, 114, 116, etc., all have operative tips in the form of sharp needle points as discussed hereinabove particularly with reference to FIG. 2B. The sharp needle tips are preferably integrally formed parts of the respective needle shafts. In such percutaneous procedures, it is not necessary for the sampling instrument to include a sheath. Thus, sheath members 99, 115, 117 are omitted.

The percutaneous core tissue sampling instrument exemplarily of FIGS. 12-14 may be used for prostrate, thyroid, parathyroid, and perhaps liver and kidney biopsy extraction, as well as in obtaining breast biopsies.

Accordingly, a method for obtaining a core biopsy specimen from a superficial organ uses an ultrasound probe to localize and delineate a suspected mass lesion in an internal organ of a patient. The method additionally comprises inserting the needle tip portion of needle shaft 98, 114, 116 through the patient's skin, pushing the needle towards and into the mass lesion under ultrasound guidance, shifting actuator handle or shifter member 94, 110, 122 in a distal direction, and during that shifting engaging the associated camming mechanism to cause a tip of the needle to rotate 360 degrees within the mass lesion, thereby severing a tissue sample from the mass lesion. Subsequently, the tissue sample is aspirated deeper into the needle (e.g., by operating a syringe), the needle is removed from the tissue, and a liquid is injected through the needle, causing the core biopsy to be ejected into a preservative solution.

It is to be further noted that any of the embodiments of a core tissue sampling instrument described and illustrated herein may be provided with an electrical connector operatively linked to the needle element for enabling the transmission of a cauterization current to a target tissue site internal to the patient. The use of cauterization is described hereinabove with reference to FIGS. 1-7.

As illustrated in FIG. 2B, any of the needle tips disclosed herein may be provided along at least a portion of its length with a plurality of longitudinally spaced apertures 134 for the dispensing of a liquid solution into internal tissues. Apertures 134 may be staggered circumferentially about the needle.

FIG. 15 is a schematic view of an upper portion of a patient's digestive tract, showing a step in an endoscopic procedure utilizing a core tissue sampling instrument 136 having an actuator subassembly 138 (as shown in FIG. 12), a flexible tubular sheath 140 with a distal end portion 142, and a flexible tubular needle shaft 144. Sheath 140 with needle shaft 144 therein is inserted through a biopsy channel (not shown) in a flexible endoscope insertion member 146. Upon locating of a target biopsy site ultrasonographically, the operator advances sheath 140 and needle shaft 144 in a distal direction through the biopsy channel so that distal end portion 142 of sheath 140 and a needle tip 148 emerge from the distal end of the endoscope insertion member 146. Needle shaft 144 is further advanced so that needle tip 148 is inserted into a target tissue mass 150 inside the patient's liver 152. Further details of this procedure are described hereinabove with reference to FIGS. 3-7.

Although the invention has been described in terms of particular embodiments and applications, one of ordinary skill in the art, in light of this teaching, can generate additional embodiments and modifications without departing from the spirit of or exceeding the scope of the claimed invention. For example, it is to be appreciated that the camming mechanism disclosed herein, including stub 38 and metal tube 41, may be used to generate a rotary motion from a longitudinal translation in other kinds of endoscopic instruments including, for instance, cauterization snare capture pockets.

Accordingly, it is to be understood that the drawings and descriptions herein are proffered by way of example to facilitate comprehension of the invention and should not be construed to limit the scope thereof.

What is claimed is:

1. A medical instrument comprising:
an elongate tubular sheath member having a diameter sufficiently small so that said sheath member is disposable in a channel of a flexed flexible endoscope, said sheath member having an opening at a distal tip, said opening extending in a plane at least partially transverse to a longitudinal axis of said sheath member;
an elongate shaft member longitudinally passing through at least a substantial portion of said elongate tubular sheath member;
an actuator handle subassembly with a manually actuated shifter member operatively connected to a proximal end of said elongate shaft member at least for longitudinally moving said shaft member;
a camming subassembly operatively connected to said shaft member and to said shifter member at least for causing said elongate shaft member to rotate during an axial motion of said shaft member, wherein said camming subassembly comprises at least one key element and at least one corresponding cutout or guide element; and
an operative element disposed at a distal end of said shaft member, said shifter member being operatively connected to said proximal end of said elongate shaft member,
wherein an axial force applied to said shifter member shifting said shifter member in an axial direction causes said shaft member and said operative element to advance in an axial direction, while concurrently effecting an at least 360° degree rotation of said operative element.

2. The medical instrument set forth in claim 1 wherein said operative element takes the form of a hollow needle member.

3. The medical instrument set forth in claim 2 wherein said hollow needle member is made at least partially of a shape memory material.

4. The medical instrument set forth in claim 1, wherein said shaft member is made, at least in part, of a shape memory metal material.

5. A medical instrument assembly comprising:
a flexible elongate shaft member with a hollow needle element disposed at a distal end thereof, wherein at least said shaft member is configured to possess shape memory;
a flexible elongate outer tubular sheath member slidably housing at least partially said elongate shaft member and said needle element, said tubular sheath member having a diameter sufficiently small so that said tubular sheath member is disposable in a biopsy channel of a flexed flexible endoscope, said sheath member having an opening at a distal tip, said opening extending in a plane at least partially transverse to a longitudinal axis of said sheath member; and
an actuator subassembly with an operator actuated shifter member operatively connected to a proximal end of said shaft member; and
a rotation-generating mechanism disposed in said actuator subassembly and operatively connected to said shaft member and to said shifter member, wherein said rotation-generating mechanism comprises at least one key element and at least one corresponding cutout or guide element,
wherein an axial force applied to said shifter member causing said shifter member to move in an axial direction causes said shaft member and said needle element to advance in the axial direction, concurrently bringing about an at least 360° degree rotation of said needle element.

6. A medical instrument assembly comprising:
a substantially rigid shaft member;
an operative needle element provided on a distal end of said shaft member, said needle element having an opening at a distal tip, said opening extending in a plane at least partially transverse to a longitudinal axis of said needle member;
an actuator handle subassembly with an operator actuated shifter member operatively connected to a proximal end of said shaft member; and
a camming subassembly disposed in said actuator handle subassembly, said camming subassembly being operatively connected to said shaft member and to said shifter member, wherein said camming subassembly comprises at least one key element and at least one corresponding cutout or guide element,
wherein an axial force applied to said shifter member causing said shifter member to shift in an axial direction causes said shaft member to advance in the axial direction, concurrently bringing about an at least 360° degree rotation of said shaft member.

7. The instrument assembly set forth in claim 6 wherein:
said shaft member is a tubular member configured with a longitudinally extending lumen; and
said operative needle element is a hollow needle tip provided at one end of said shaft member, said needle tip extending in a direction away from said one end of said shaft member.

8. The instrument assembly set forth in claim 6 wherein said camming subassembly includes a spiral-shaped element.

9. The medical instrument set forth in claim 1 wherein one of said key element and said cutout or guide element is affixed directly or indirectly to one of (a) said elongate shaft member and (b) a member of said actuator handle subassembly.

10. The medical instrument set forth in claim 9 wherein a manually induced axial motion of said shifter member of said actuator handle subassembly engages said key element member with said cutout or guide element, thereby causing said shaft member to simultaneously advance and execute at least a 360° rotation.

11. The medical instrument set forth in claim 9 wherein said key element is taken from the group consisting of a stub and a flange or rib having a helical shape.

12. The medical instrument set forth in claim 1 wherein said shaft member is made at least partially of braided stainless steel.

* * * * *